United States Patent [19]

Galwey et al.

[11] 4,227,988
[45] Oct. 14, 1980

[54] POTENTIOSTAT FOR USE WITH ELECTROCHEMICAL CELLS

[75] Inventors: Ronald K. Galwey, Los Gatos; Kay K. Kanazawa, San Jose, both of Calif.

[73] Assignee: International Business Machines Corporation, Armonk, N.Y.

[21] Appl. No.: 25,415

[22] Filed: Mar. 30, 1979

[51] Int. Cl.³ .............. C25B 15/02; G01N 27/30; G05F 1/10; H02H 9/00
[52] U.S. Cl. .................. 204/231; 204/195 F; 323/9; 361/18; 361/93
[58] Field of Search ............ 204/231, 195 R, 195 F, 204/228; 323/9; 361/18, 93

[56] References Cited

U.S. PATENT DOCUMENTS

| | | | |
|---|---|---|---|
| 3,428,532 | 2/1969 | Banks | 204/195 R |
| 3,616,286 | 10/1971 | Aylward et al. | 204/228 X |
| 3,855,101 | 12/1974 | Wilson | 204/195 R |
| 4,028,207 | 6/1977 | Faktor et al. | 204/195 R |
| 4,059,406 | 11/1977 | Fleet | 204/195 R |
| 4,134,808 | 1/1979 | Krüger et al. | 204/228 X |

*Primary Examiner*—John H. Mack
*Assistant Examiner*—D. R. Valentine
*Attorney, Agent, or Firm*—Joseph E. Kieninger

[57] ABSTRACT

An improved potentiostat for use with electrochemical cells provides dynamic protection of both the electrochemical cell elements and the sensitive potentiostat components from any significant voltage or current overload. A comparator compares the potentiostat input voltage with the electrochemical cell reference electrode voltage. When the reference electrode voltage becomes substantially different from the potentiostat input voltage and exceeds a certain preset value, the comparator activates a control means that causes the cell current to go to zero. This system provides dynamic protection even as the input voltage varies.

9 Claims, 1 Drawing Figure

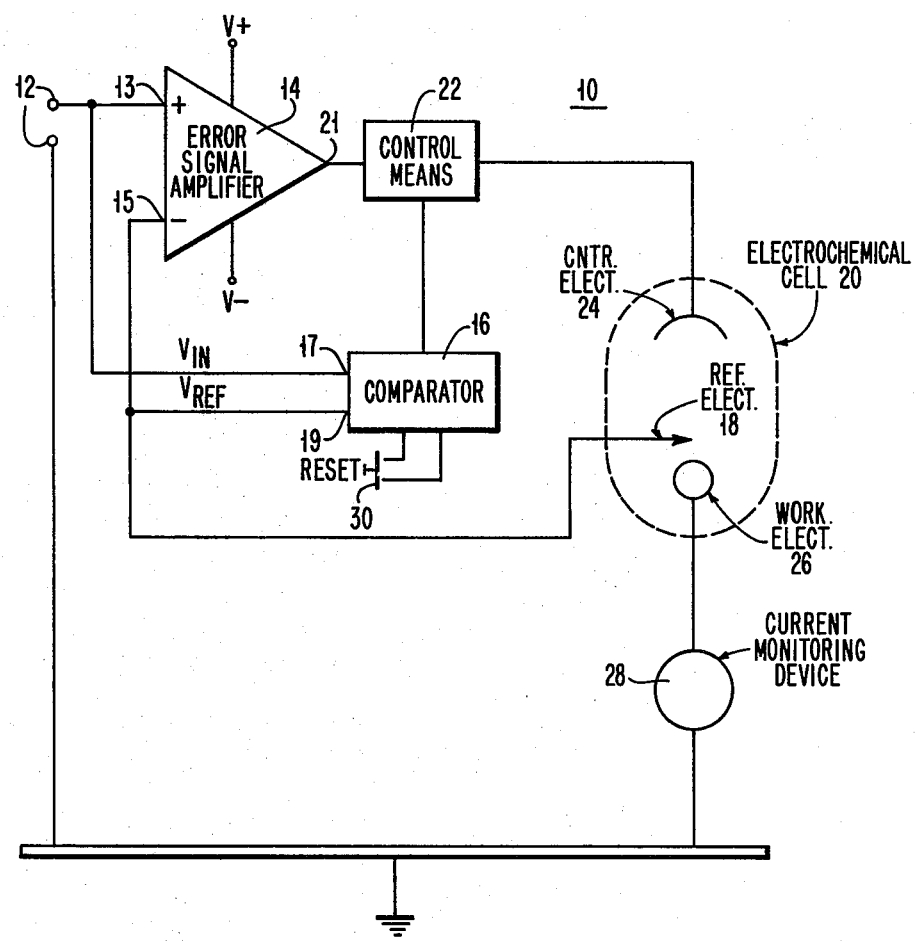

POTENTIOSTAT FOR USE WITH ELECTROCHEMICAL CELLS

DESCRIPTION

1. Technical Field

This invention relates to an improved potentiostat for use with electrochemical cells and more particularly to a control system which protects the potentiostat and the electrochemical cell from electrical damage.

It is a primary object of this invention to provide a dynamic protection system for electrochemical potentiostat-cell systems.

It is another object of this invention to provide improved potentiostat for use with electrochemical cells.

It is yet another object of this invention to provide a dynamic control system for protecting an electrochemical cell and a potentiostat from electrical damage.

It is a still further object of this invention to provide a dynamic control system for protecting electrochemical potentiostat-cell systems from being operated in a manner that is beyond the electrochemical potentiostat-cell system's capability.

It is yet a still further object of this invention to sense the loss of control in the electrochemical potentiostat-cell system before damage sets in.

2. Background Art

Electrochemical cells are widely used for electrochemical and biological applications. Typically, electrochemical cells have a working electrode, a non-current carrying reference electrode and a counter electrode. Controlling and measuring the electrical parameters of an electrode reaction in a cell is done by potential, current and charge control methods.

A review article by R. Greef covering this subject matter is published in the Journal of Physics E: Scientific Instruments, Vol. 11, 1978, pages 1–12 (printed in Great Britain). Many control methods utilize potential and as a result are referred to as potentiostatic control systems for electrochemical cells or electrochemical potentiostat-cell systems.

Modern potentiostatic control systems for electrochemical cells usually use operational amplifiers in a feedback control configuration. This feedback is used to control the potential of the cell's non-current carrying reference electrode potential relative to the cell's working electrode potential. The stability of this control system depends upon the details of the cell geometry and cell chemistry as well as on the details of the electronic circuitry. Loss of control in this feedback control system may or may not be accompanied by an outright instability. Loss of control without instability occurs when the bandwidth limitations of the system are exceeded. When instability occurs in the system, it results in either system saturation or oscillation. With system saturation, a large constant potential and current is applied to the cell, whereas with oscillation, a large, uncontrolled oscillatory voltage and current is applied to the cell. In addition to possible damage to electronic components, the application of such large potentials and currents across the cell can alter and even damage the physical and chemical composition of the cell.

Attempts to minimize the effects of such instabilities in the past have frequently taken the form of overload indicators, typically in the form of lights. These lights are activated by circuitry sensing excessive potentials and/or currents in the cell. These limits can be set to prevent permanent damage to sensitive electronic components. Of course, when these lights are activated due to a system instability, the system has already passed from its linear control state to its non-linear, unstable state. Even though the circuitry may include elements to disconnect the cell under these conditions, the short period of overload conditions can be sufficient to cause irreparable damage to sensitive cells. Examples of cell configurations which would be particularly vulnerable to such overloads would be cells for microanalysis, cells with fragile thin-film metal electrodes, cells using surface modified electrodes and thin cells.

Electrochemical potentiostat-cell systems also require protection on occasion from being operated in a manner that is beyond the system's capability. For example, the operator may inadvertently apply an input signal whose frequency exceeds the bandwidth limitations of the potentiostat-cell system. It is difficult to know while the operator is obtaining the data that he is exceeding the potentiostat-cell system's capabilities.

BRIEF DESCRIPTION OF THE DRAWING

The accompanying drawing forms a material part of this disclosure and is an electrical block diagram showing the various elements comprising the potentiostatic control system of this invention.

DISCLOSURE OF THE INVENTION

For a further understanding of the invention and of the objects and advantages therefor, reference will be had to the following description and accompanying drawing, and to the appended claims in which the various novel features of the invention are more particularly set forth.

An improved potentiostat for use with electrochemical cells provides dynamic protection of both the electrochemical cell elements and the sensitive potentiostat components from any significant voltage or current overload. The system is also protected from being operated in a manner that is beyond the electrochemical potentiostat-cell system's capability. A comparator compares the potentiostat input voltage with the electrochemical cell reference electrode voltage. When the reference electrode voltage becomes substantially different from the potentiostat input voltage and the magnitude of the difference between these values exceeds a certain preset value, the comparator activates a control means that causes the cell current to go to zero. This system provides dynamic protection even as the input voltage varies.

BEST MODE FOR CARRYING OUT THE INVENTION

As shown in the drawing, the electrochemical potentiostat-cell system 10 has an external input voltage $V_{IN}$, 12. The external input voltage 12 is of the order of 0 volts up to $\pm 5$ volts and is of the type well known in the industry. For example, the voltage may take the form of DC voltages, ramp voltages, pulse voltages, sinusoidal voltages, and the like. The input voltage 12 is connected to the non-inverting input 13 of error signal amplifier 14 and to the input 17 of the comparator 16. The error signal amplifier 14 is a conventional operational amplifier. The inverting input 15 of error signal amplifier 14 is connected to the reference electrode 18 of the electrochemical cell 20. The reference electrode 18 is connected to input 19 of the comparator 16. The comparator 16 may be, for example, a window comparator consisting of a difference amplifier whose output is compared with preset limits by a limit sensor.

The voltage output 21 of the error signal amplifier 14 is connected through a control means 22 to the counter electrode 24 of cell 20. The error signal amplifier provides voltage at counter electrode 24 to cause sufficient current flow through the cell 20 such that the potential of the reference electrode 18 is equal to the voltage input 12 whenever the potentiostat-cell system is operating within its capabilities. The cell current flows through the working electrode 26 through a current monitoring device 28 such as, for example, an ammeter, to ground.

The comparator 16 senses the potential of the reference electrode 18 and compares that value to the input 12 of the potentiostat. When the voltage limits of the comparator 16 are exceeded by the magnitude of the difference between $V_{IN}$ and $V_R$, the comparator causes the control means 22 to cause the cell current to go to zero. This in effect forms a protective control loop which functions dynamically even as the potentiostat-cell system's characteristics change due to variations in the cell behavior arising from potential variations. The control means 22 may be an electromechanical switch or a current controlling transistor, i.e. a transistor operated as an electronic switch. Other conventional switching means may also be employed. A reset switch 30 is provided to reactivate the system after the control means has activated and subsequent correction action has been taken to eliminate the problem.

INDUSTRIAL APPLICABILITY

The advantages of the protection system made in accordance with this invention are that it provides dynamic protection against loss of control caused by either instability in the potentiostat-cell system or by operating outside the capabilities of that system. This system protects against improper operation by inexperienced operators or by inadvertent faulty connection to the cell. This system is particularly useful for cells used for microanalysis, for cells containing fragile thin-film metal electrodes and for thin cells which are particularly vulnerable to overloads which cause irreparable damage. This protection system is also useful in automated analytical systems where no operator may be present. This system protects not only the electrochemical cell, but it also protects the electronic components in the potentiostat.

While the invention has been particularly shown and described with reference to a preferred embodiment thereof, it will be understood by those skilled in the art that various changes in the form and details may be made therein without departing from the spirit and scope of the invention.

We claim:

1. A dynamic protection system for an electrochemical potentiostat-cell system having an input voltage $V_{IN}$ and a reference electrode with a potential $V_R$ comprising
   control means associated with the cell system, and
   a comparator associated with said control means for comparing the difference between $V_R$ and $V_{IN}$ wherein when the magnitude of the difference between the values of $V_{IN}$ and $V_R$ exceeds a preselected value said control means causes the current in the cell to go to zero.

2. A protection system as described in claim 1 wherein said control means is an electronic switch.

3. A protection system as described in claim 1 wherein said control means is an electromechanical switch.

4. A protection system as described in claim 1 including reset means associated with said comparator.

5. A potentiostat for use with an electrochemical cell having an input voltage $V_{IN}$ and a reference electrode with a potential $V_R$ comprising
   control means associated with said input voltage means and the cell, and
   a comparator associated with said control means for comparing the difference between $V_R$ and $V_{IN}$ wherein when the magnitude of the difference between the values of $V_{IN}$ and $V_R$ exceeds a preselected value, said control means causes the current in the cell to go to zero.

6. A potentiostat as described in claim 5 including an error signal amplifier connected between the input voltage and said control means.

7. An electrochemical potentiostat-cell system comprising
   an electrochemical cell having a reference electrode with a potential $V_R$,
   a potentiostat associated with said cell and having an input voltage $V_{IN}$,
   control means electrically connected to said cell, and
   a comparator for comparing the difference between $V_R$ and $V_{IN}$ associated with said control means wherein when the magnitude of the difference between the values of $V_{IN}$ and $V_R$ exceeds a preselected value, said control means causes the current in said cell to go to zero.

8. An electrochemical potentiostat-cell as described in claim 7 wherein said control means is a switch.

9. An electrochemical potentiostat-cell as described in claim 7 including a current monitoring device associated with said cell.

* * * * *